(12) United States Patent
Sherman

(10) Patent No.: US 6,371,945 B1
(45) Date of Patent: Apr. 16, 2002

(54) EYE DROPPER POSITIONING DEVICE

(76) Inventor: Thomas Sherman, 4730 E. Indian School Rd. #120, Phoenix, AZ (US) 85018

( * ) Notice: Subject to any disclaimer, the term of this patent is extended or adjusted under 35 U.S.C. 154(b) by 0 days.

(21) Appl. No.: 09/817,047

(22) Filed: Mar. 27, 2001

(51) Int. Cl.[7] ............................................. A61H 33/04
(52) U.S. Cl. ...................................... 604/302; 604/300
(58) Field of Search ............................ 604/295–302, 604/294; 222/420–422

(56) References Cited

U.S. PATENT DOCUMENTS

| | | | | |
|---|---|---|---|---|
| D249,709 S | * | 9/1978 | Trovinger | 604/300 |
| 4,134,403 A | * | 1/1979 | Johnsen et al. | 604/300 |
| 4,257,417 A | * | 3/1981 | Gibilisco | 604/300 |
| 4,605,398 A | * | 8/1986 | Herrick | 604/300 |
| 4,685,906 A | * | 8/1987 | Murphy | 604/300 |
| 4,834,727 A | * | 5/1989 | Cope | 604/300 |
| 4,960,407 A | * | 10/1990 | Cope | 604/300 |
| 5,848,999 A | * | 12/1998 | Basilice et al. | 604/300 |
| 6,090,086 A | * | 7/2000 | Bolden | 604/302 |

\* cited by examiner

*Primary Examiner*—Dennis Ruhl
(74) *Attorney, Agent, or Firm*—The Halvorson Law Firm

(57) ABSTRACT

The present invention is directed to a device that aids in the placement of eye drops from an ophthalmic medication containing bottle. The device of the present invention is designed to be attached to the bottle at all times, including while in use. Furthermore, the present invention is specifically designed to aid in the easy removal and replacement of ophthalmic solution containing bottle caps. The present invention, in its most basic form, comprises an eye ring, a bottle attaching portion, wherein the eye ring and flexible extension may be moved off of the bottle axis to permit easy removal and replacement of the bottle cap.

4 Claims, 5 Drawing Sheets

EYE DROPPER POSITIONING DEVICE

FIELD OF THE INVENTION

The present invention relates to the ophthalmic solution dispensing devices, and has particular reverence to a novel construction for an eyedropper positioning guide that works in combination with an ophthalmic medicament bottle, which includes a dispensing nozzle.

BACKGROUND OF THE INVENTION

A common malady that affects eyes is that they become irritated due to dust and small foreign objects that are common pollutants in the air. One method for alleviating this irritation is the application of an eye wash, a liquid medicament, to the eyes. Most eye washes are contained in a bottle that incorporates a dropper mechanism in the top. However, these eye droppers are difficult to operate. Most people have difficulty in applying drops due to the extreme sensitivity of their eyes. Moreover, poor vision makes it difficult to properly opposition or align an eye dropper bottle relative to the eye frequently causes drops to be improperly applied. Thus, the user quite often wastes eyewash by missing the intended eyeball.

Thus, applying eye drops is generally difficult, uncomfortable and results in little, if any, of each drop entering the eye so that several attempts are necessary to insure placement of the ophthalmic solution in the eye. As a result, considerable amounts of the solution are wafted with no real assurance that a prescribed or desired amount of solution was placed in the eye.

Another common and potentially injurious problem occurs when the applicator tip accidentally comes in contact with the corneal surface. This problem is especially serious in individuals with physical or neurological limitations causing unsteady hand movements.

Generally, there is a line of eye drop guiding devices that may be attached to bottles containing ophthalmic medication. These bottles consist primarily of a fluid containing portion, a neck, a fluid dispensing portion, and a bottle cap. The available devices, basically, are comprised of a bottle attaching portion, an eye ring, and some form of rigid extension piece connecting the bottle attaching portion to the eye ring. However, these devices are constructed more with the actual end use of the device in mind, and not with the convenience and functionality of pre and post usage.

One difficulty with using the available eye drop guides is removing the cap of the attached bottle. The extension pieces of these devices are of rigid, unyielding construction and one would have to have the manual dexterity of a magician to comfortably remove the bottle cap without first removing he eye drop guide from the bottle.

Therefore, it is the primary purpose of the present invention to provide a simplified and easily attached add-on device that works in combination with existing eyedroppers to guide the user in properly placing ophthalmic medication. It is a further purpose of the present invention to provide an eye drop guide device that facilitates the removal of a bottle cap prior to use and while the device is simultaneously attached to the bottle.

PRIOR ART

The prior art reveals several different types of eye drop directing apparatus. These range from replacement caps including special features to bottle attachments that hold the eyelid in place while simultaneously guiding the eye drops into the eye.

U.S. Pat. No. 5,387,202, by Baron, shows an eye drop dispensing device that consists essentially of a flexible tube of oval cross section that is placed over the body of a pliable ophthalmic solution container. Located at the base of the oval tube is a rim to aid in holding an eyelid in place during the application of the medication. The tube, and the enclosed pliable ophthalmic solution bottle, is simultaneously squeezed to apply the solution to the eye while the user is looking along the oval channel f the device. This device must be repeatedly removed and reattached in order to access the bottle cap.

U.S. Pat. No. 3,872,866, by Lelicoff, teaches a device that includes a ring for attaching the device to a bottle, an end piece for engaging a user's eyelid during the application of ophthalmic solution, and an inwardly curved extension piece attached to a boss on the ring. The curved extension piece is designed to aid in the placement of applied drops of medicated solution. The eye engaging portion of this device interferes with easy removal of the bottle cap.

U.S. Pat. Nos. 4,834,727 and 4,960,407, bot by Cope, disclose a series of eye dropper bottle attachments. All of the embodiments utilize an oval eyelid retaining ring. The bottle is attached to the ring by either a single extension piece or a set of two extension pieces. The primary difference in the several embodiments of these two patents lies in the many different ways in which the device is attached to a bottle. One embodiment illustrates a split ring configuration wherein a ring is bisected to relate two arcuate pieces, each attached to a separate extension piece. A second embodiment is a hook ring attachment wherein the hook grasps the bottle at the neck of the bottle. This hook attachment is attached to the eyelid ring by a sing rigid extension piece. Another embodiment of these patents is an oval eyelid ring that is attached by two rigid extension poles to the neck ring of the device. A final embodiment illustrated by this patent shows the attachment of a singular oval eyelid ring to the neck ring by an extendible rigid extension piece. All of the embodiments of these patens have rigid extension pieces. Furthermore, their very design interferes with easy access to the bottle cap.

While these patents accomplish many fine results, they do not address the problem of removal and replacement of the cap of the ophthalmic solution containing bottle. The above eye drop guiding devices all include rigid extension pieces and eyelid grasping attachments that are located in close proximity to the cap of the bottle. The close location of these features makes it difficult to remove the bottle cap before use and replace the cap after use. This impediment to removal and replacement of the bottle cap frustrates the use and encourages the user to leave the cap off, thus creating a potentially unsanitary condition within the bottle containing ophthalmic solution.

SUMMARY OF THE INVENTION

It is an object of the present invention to provide an instrument that is easily and quickly attached to a plastic eye dropper bottle to increase accuracy in dispensing ophthalmic solutions in post-surgical and general use.

It is another object of the present invention to provide a device that allows for the easy removal and replacement of a bottle cap while the device is attached to the bottle.

It is still yet another object of the present invention to provide a device that includes a positioning indicator for the proper placement of an eye drop guide when attaching the guide to a bottle containing ophthalmic solution.

It is a further object of the present invention to provide a device that includes a flexible extension portion that allows the user to easily remove and replace the cap of a bottle by displacing the eyelid engaging ring off axis from the bottle.

It is still a further object of the present invention to provide a method for easy removal and replacement of a bottle cap while an eye drop guiding device is attached to the bottle.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

The novel features that are considered characteristic of the invention are set forth with particularity in the appended claims. The invention itself, however, both as to its structure and its operation together with the additional objects and advantages thereof will best be understood from the following description of the preferred embodiment of the present invention when read in conjunction with the accompanying drawings wherein:

DETAILED DESCRIPTION OF THE INVENTION

Referring now to the figures, the present invention provides an eye drop guidance device that, when attached to a bottle with a cop, allows easy removal and replacement of the cap. The device of the present invention is simpler to construct and especially simpler to use than any devices thus discovered in the prior art. This simplicity is especially evident when it is understood that the device of the present invention may not only be used with two hands as all eye drop positioning guides are, but with a single hand, if necessary. This feat is nearly impossible with many of the prior art devices.

Figure 1:
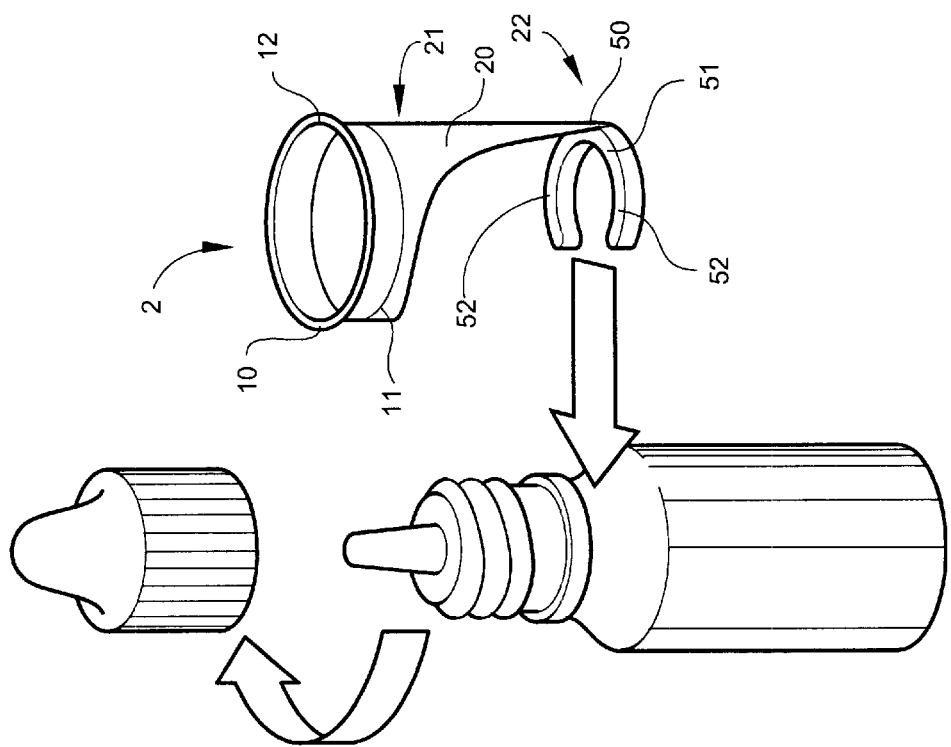
FIG. 1 illustrates the attachment of a first embodiment of the present invention to a bottle containing ophthalmic solution.

FIG. 1 illustrates a first preferred embodiment 1 of the present invention. The device has an oval, or rounded rectangular eyelid engaging ring 10. The ring 10 has a support flange 11 attached to a backside that runs along the entire periphery of the ring 10. A flexible extension piece 20 is attached to the support flange 11 at a first end 21. The flexible extension piece 20 is preferably attached along a long side 12 of the oval shape of the eyelid engaging ring 10. Furthermore, there is, attached at a second end 22 of the extension piece 20, a bottle attaching portion 30. As can be seen from FIG. 1, the bottle attaching portion 30 of the first preferred embodiment 1 comprises a pair of arms 31 extending transverse to the direction of the extension piece 20 at opposite sides 23 of the extension piece 20. Applied to an inner surface 32 of the pair of arms 31, and on an inner surface 24 of a portion of the second end 22 of the extension piece 20, is adhesive. The adhesive is protected from pre-use contamination by a thin covering 33, typically paper or a wax paper material. Finally, there are position indicators 35 placed on either an inside or outside surface of the device 1. By selecting a clear plastic material, neither inside or outside surface is preferable over the other.

Figure 1B:
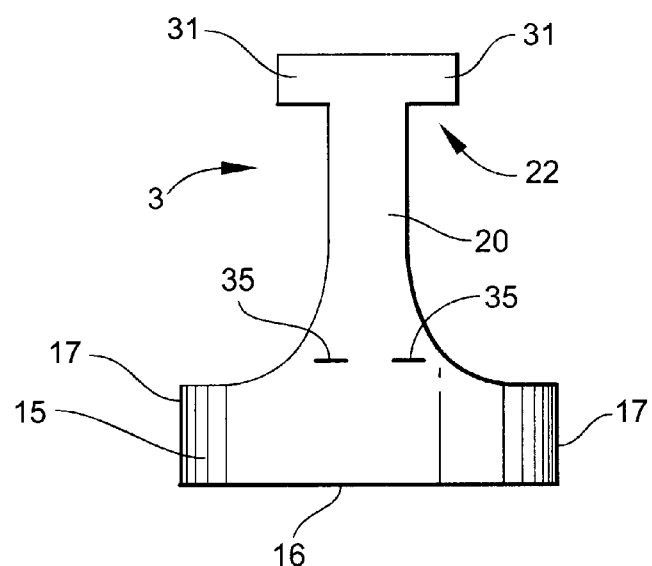
FIG. 1B depicts the shape of thin flexible plastic used to construct the first preferred embodiment.

One method of constructing the first preferred embodiment 1 is to take a piece of thin flexible plastic material and cut a shape 3 as illustrated in FIG. 1B. On the shape is a substantially rectangular base potion 15. One long side of the base portion 15 gradually extends outward to form the extension piece 20. When looking at the base portion 15 and extension piece 20, they appear to form a T-shape wherein the junction of the T is a smooth and continuous curve, as opposed to discontinuous. The extension piece 20 has at the second end 22, two small rectangular arms 31 projecting transverse to the long direction of the extension piece 20. The eyelid engaging ring 10 is formed by rolling a lower end 16 of the base 15, preferably with the roll directed to an outside surface of the plastic material. The roll does not consume the entire width of the base portion 15, since the unused portion forms a support flange 11 that runs along the periphery of the eyelid engaging ring 10. Opposite outside ends 17 of the base 15 are then attached to each other to form the ring 10 itself. The position indicators 35 are then attached to each other to form the ring 10 itself. The position indicators 35 are then placed on the extension piece 20 or the support flange 11 at a position where the dispensing end of a bottle should be located. Alternately, device 1 may be manufactured by injection molding techniques or other similar plastic shaping technologies.

When using the first preferred embodiment 1, the user will remove the protective covering 33 from the applied adhesive. The user will then align the bottle to the device 1 with the position indicators such that the tip of the dispensing portion of the bottle is properly placed relative to the eyelid engaging ring 10. The user then firmly applies the attaching section 30, with the adhesive located on the inside, to the bottle. This, then, firmly attaches the first preferred embodiment 1 to the bottle.

Figure 2:
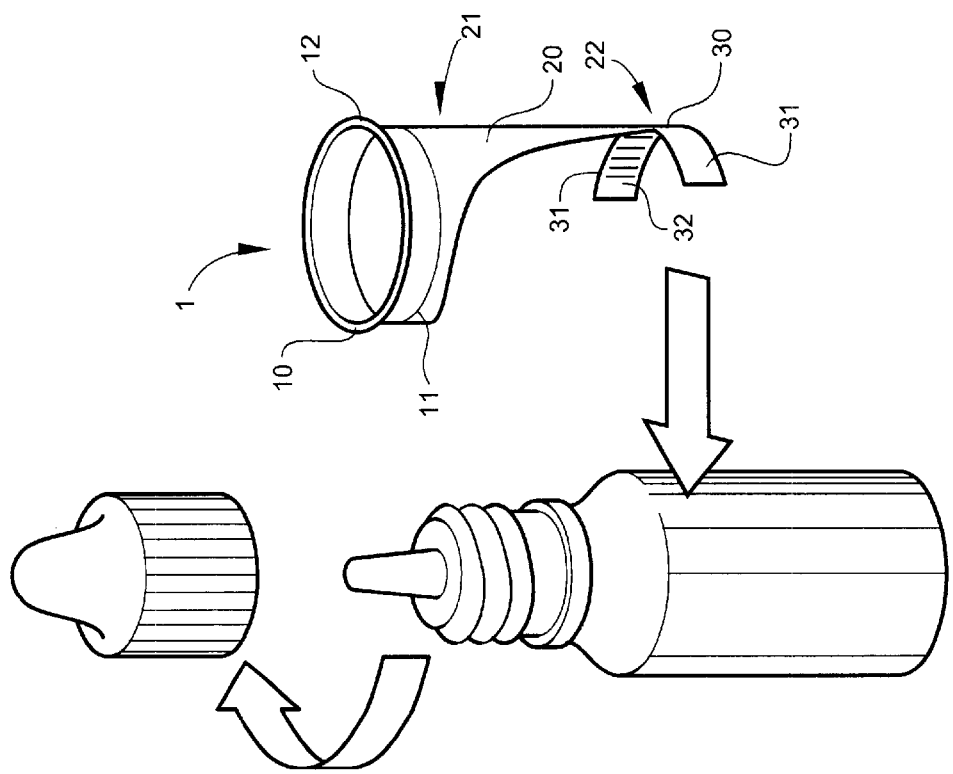
FIG. 2 illustrates the attachment of a second embodiment of the present invention to a bottle containing ophthalmic solution.

FIG. 2 illustrates a second preferred embodiment 2. The device of the second preferred embodiment 2 also has an oblong, or rounded rectangular shaped eyelid engaging ring 10. The ring 10 has a support flange 11 attached to a backside that runs along the entire periphery of the ring 10. A flexible extension piece 20 is attached to the support flange 11 at a first end 21 of the extension piece 20. The flexible extension piece 20 is preferably made from a thin, flexible plastic material. The extension piece 20 should be attached along a long side 12 of the oval shape of the eyelid engaging ring 10. Furthermore there is, attached at a second end 22 of the extension piece 20, a bottle attaching portion 50. As can be seen from FIG. 2, the bottle attaching portion 50 of the second preferred embodiment 2 is a C-shaped semi-rigid piece of plastic. The C-shaped bottle attaching portion 50 is formed by a thickened base portion 51 with a pair of inwardly curved arms 52 attached at opposite ends 53 of the base portion 51. The base portion 51 is attached to an inner surface 24 of the extension piece at a backside of the base portion 51.

Figure 2B:
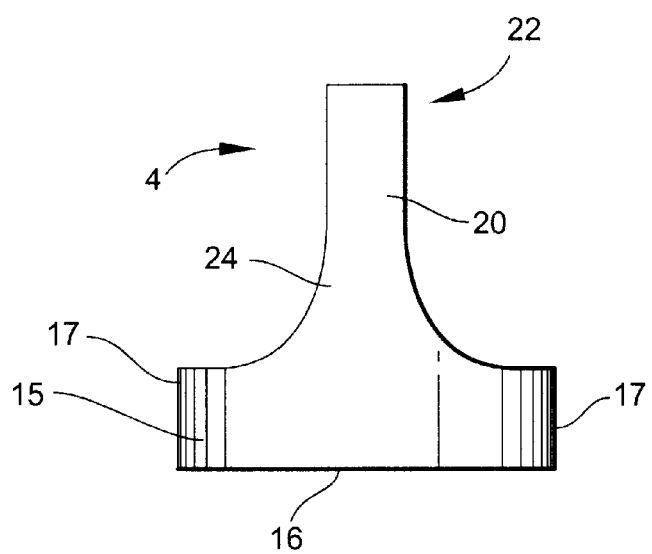
FIG. 2B depicts the shape of thin flexible plastic used to construct the second preferred embodiment.

One method of constructing the second preferred embodiment 2 is to take a piece of thin flexible plastic material and cut a T-shape 4 as illustrated in FIG. 2B. The T-shape comprises a substantially rectangular base portion 15. One long side of the base portion 15 gradually extends outward to form the extension piece 20. When looking at the base portion 15 and extension piece 20, the junction of the T forms a smooth and continuous curve, as opposed to discontinuous. The eyelid engaging ring 10 is formed by rolling a lower end 16 of the base 15, preferably with the roll directed to an outside surface of the plastic material. The roll does not consume the entire width of the base portion 15, since the unused portion forms the support flange 11 that runs along the periphery of the eyelid engaging ring 10. Opposite outside ends 17 of the base 15 are then attached to each other to form the ring 10 itself. Alternately, device 2 may be manufactured by injection molding techniques or other similar plastic shaping technologies.

For both the first and second embodiments 1 and 2 it is important to note that the flexibility of the extension piece 20 is important. If extension piece 20 is too flexible, then when the ring 10 is pulled off axis and released, it will not return to its original position. Similarly, if the extension piece 20 is too rigid, pulling the ring off axis sufficiently far to allow access to the bottle cap will irreversibly deform the materials of the extension piece 20. Once irreversibly deformed, it will not regain it original configuration. Thus, it can be seen that there is a range of flexibility that is useful for the materials that the extension piece is produced. Accordingly, since the preferred embodiment of the present invention is made from Acetal (otherwise known as Delrin) and Acetal has a flexural yield strength ranging from 5000 to 20,000 psi, it is critical that the first and second preferred embodiments 1 and 2 be made from a material that has a flexural yield strength ranging from 5000 to 20,000 psi, preferably between 10,000 and 15,000 psi, and more preferably between 13,000 and 15,000 psi.

In use, as illustrated in FIG. 2, the bottle attaching piece 50 is simply clipped onto an area of the ophthalmic solution containing bottle near the neck. The semi-rigidity of the C-shaped bottle attaching portion 50 is necessary to allow repeated attachment and removal of the device from the bottle. The cap of the bottle may then be removed and replaced as described above in the first preferred embodiment.

Figure 3:
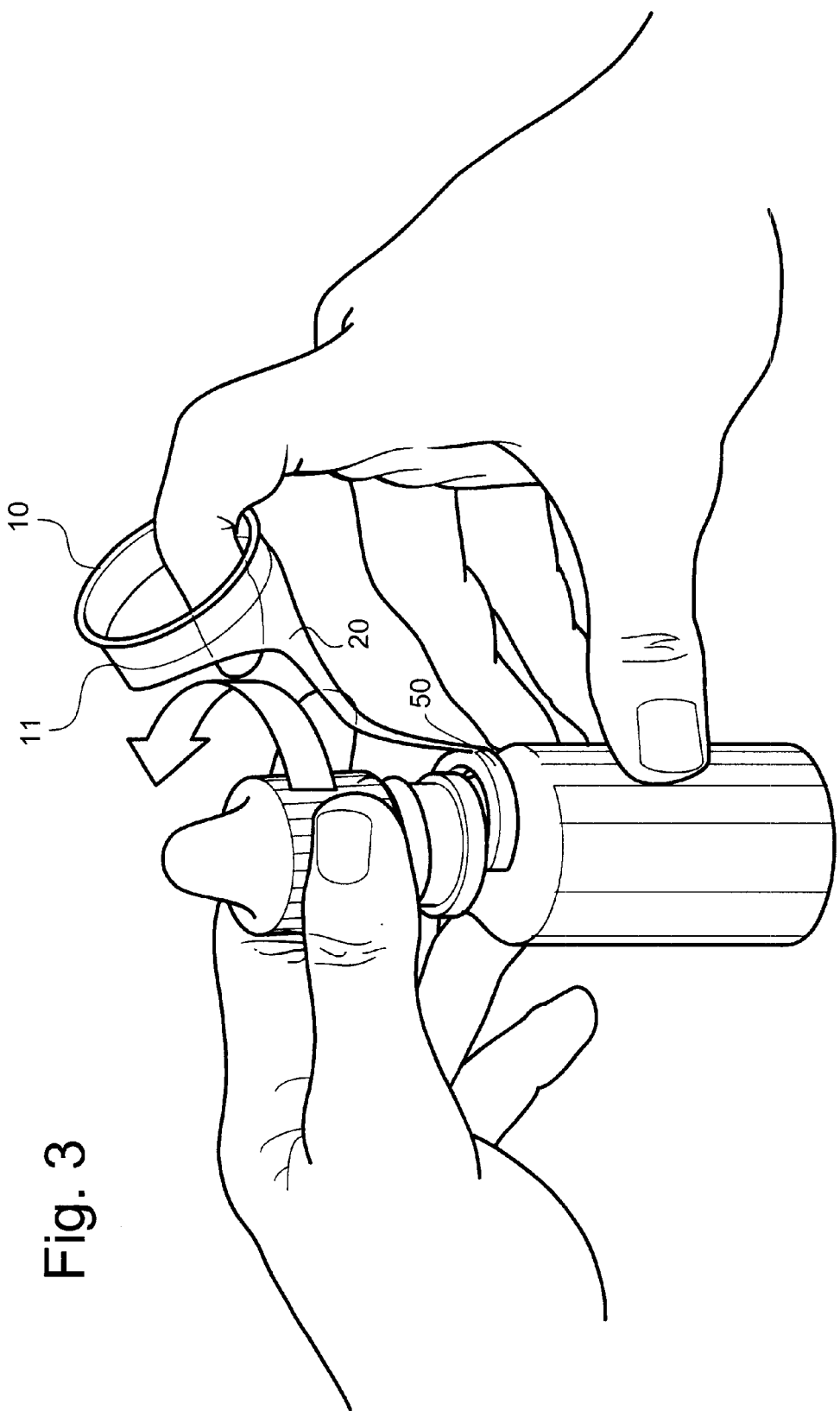
FIG. 3 depicts the removal of a bottle cap by displacing the eyelid engaging ring from the bottle axis.

In order to use the bottle with the device 1 or 2 attached, the user will grasp the bottle in a first hand with the bottle oriented in an upward position. The user then grasps the eyelid retaining ring 10 with a finger of the first hand, frequently this will be the index finger. The user then pulls back on the eyelid remaining ring 10 with the finger, thus displacing the ring 10 from axial alignment with the bottle. This displacement temporarily removes the obstructive effect of the extension piece 20 and eyelid retaining piece 10. The user may then remove the bottle cap with a second hand. Once the bottle cap is removed, the eyelid retaining ring may then be allowed to regain its former position by releasing the finger grasp, thus causing the flexible extension piece 20 to automatically return to the desired alignment with the applicator tip of the bottle. This is illustrated in FIG. 3.

Figure 4:
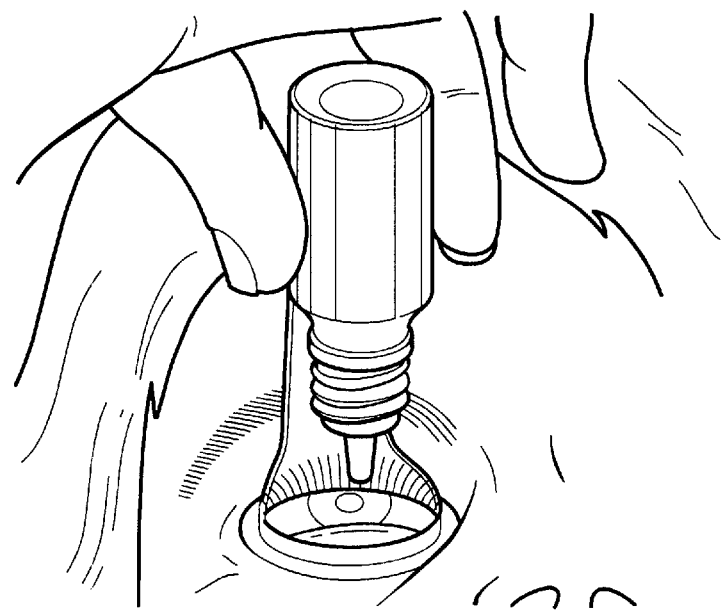
FIG. 4 shows the device guiding eye drops into an eye of a user.

The eyelid retaining ring 10 is then placed over the eye, preferably with a portion of the ring 10 frictionally holding the eyelid in an open position. The head is then tilted backward and the user gazed upward at the dispensing portion of the bottle. The bottle is gently squeezed, thereby applying an amount of ophthalmic solution onto the eye. See FIG. 4.

Figure 5:
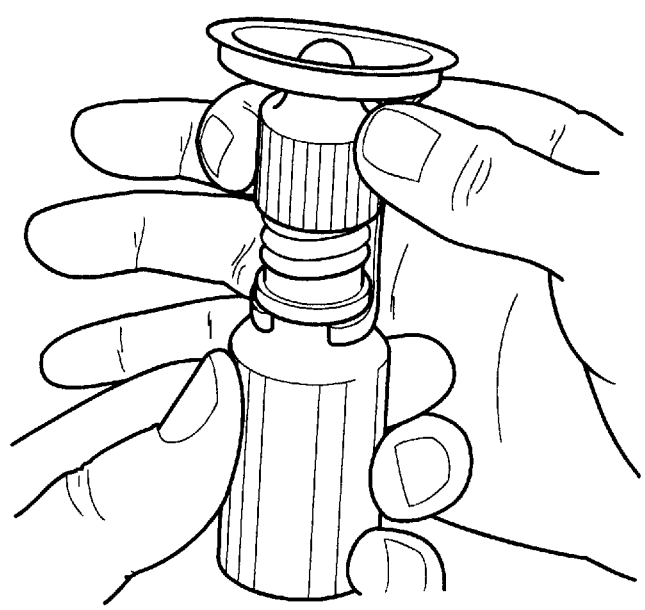
FIG. 5 depicts the replacement of the bottle cap.

Once the solution is applied, the cap replaced onto the bottle, FIG. 5, and the attached device 1 or 2 may then be removed, and once again placed into an upright position. The user then, holding the bottle in the first hand, once again grasps the eyelid retaining ring 10 with the finger and displaces the ring off axis of the bottle. The second hand then replaces the bottle cap. The eyelid retaining ring 10 is finally, once again, allowed to regain its original position by releasing the finger's grasp.

Figure 6:
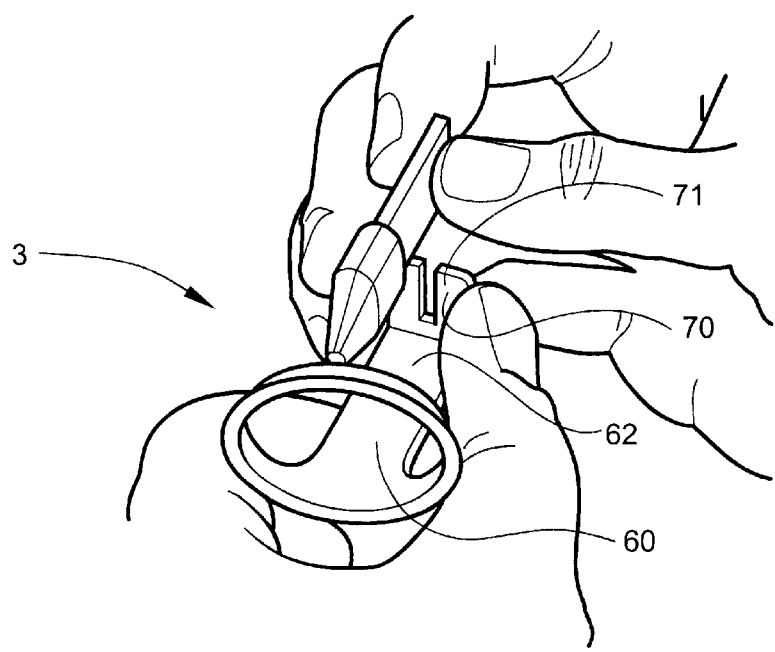
FIG. 6 illustrates a third embodiment of the present invention being attached to a single use bottle.
Figure 7:
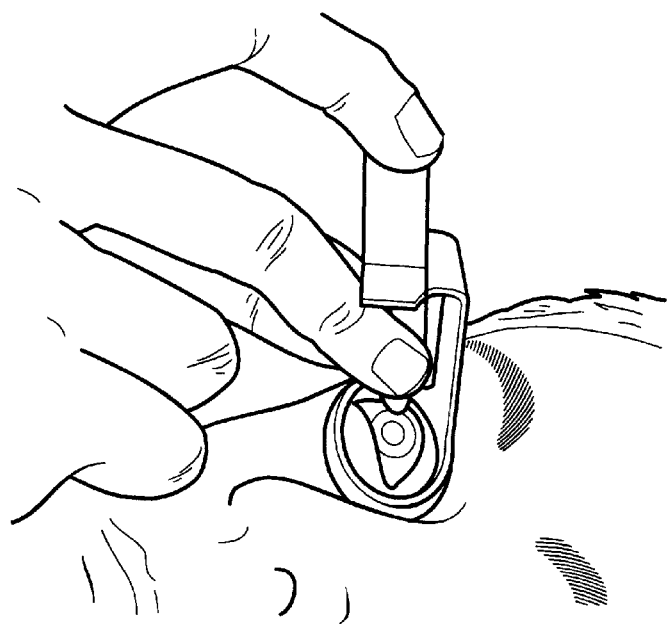
FIG. 7 shows the third embodiment of the present invention guiding eye drops into an eye of a user.

FIG. 6 illustrates a third preferred embodiment 3. The device of the third preferred embodiment 3 also has an oblong, or rounded rectangular shaped eyelid engaging ring 10. The ring 10 has a support flange 11 attached to a backside that runs along the entire periphery of the ring 10. A substantially rigid extension piece 60 is attached to the support flange 11 at a first end 21 of the extension piece 60. The substantially rigid extension piece 60 is preferably made from a thin, substantially rigid plastic material. The extension piece 60 should be attached along a long side 12 of the oval shape of the eyelid engaging ring 10. Furthermore there is, attached at a second end 62 of the extension piece 60, a bottle attaching portion 70. As can be seen from FIGS. 6 and 7, the bottle attaching portion 70 of the third preferred embodiment 3 is a substantially rigid base portion 71 that is generally perpendicular to the extension piece 60. The base portion 71 of the bottle attaching portion includes a slit that is sized to receive a disposable bottle having a flat handle portion. This type of bottle is common in the industry and is clearly illustrated in FIG. 5. Alternately, there may be a generally round insert having a slit sized to receive a disposable bottle having a flat handle portion that snuggly fits within the C-shaped bottle attaching portion 50 of the second embodiment. The base portion 71 is attached to an inner surface 24 of the extension piece at a backside of the base portion 71.

One long side of the base portion 15 gradually extends outward to form the extension piece 60. When looking at the base portion 15 and extension piece 60, the junction of the T forms a smooth and continuous curve, as opposed to discontinuous. There is a support flange 11 that runs along the periphery of the eyelid engaging ring 10. Opposite outside ends 17 of the base 15 are attached to each other to form the ring 10 itself. Preferably, device C may be manufactured by injection molding techniques or other similar plastic shaping technologies.

In use, the bottle attaching piece 70 is simply clipped onto an area of the ophthalmic solution containing bottle near the flat handle portion, typically between the flat handle portion and the solution container. Typically, at this position the bottle is narrower than the solution cavity or the flat handle portion, i.e., it is crimped. The bottle attaching portion 70 should be substantially rigid to allow repeated attachment and removal of the device from the bottle.

In order to use the bottle with the device 3 attached; the user will grasp the bottle in a first hand with the bottle with attached eye guide oriented in an upward position. The eyelid retaining ring 10 is then placed over the eye, preferably with a portion of the ring 10 frictionally holding the eyelid in an open position. The head is then tilted backward and the user gazed upward at the dispensing portion of the bottle. The bottle is gently squeezed, thereby applying an amount of ophthalmic solution onto the eye. Once the solution is applied, the bottle and attached device 3 may then be removed, and once again placed into an upright position. This may be repeated or the disposable bottle removed from the eye guide and disposed.

The preferred embodiment(s) of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A device for applying ophthalmic solutions comprising an eye guide, a substantially rigid extension portion attached to the eye guide, and a bottle attaching portion attached at a second end of the extension portion, said bottle attaching portion further comprises a base portion attached to the substantially rigid extension portion, the base portion including a slit that is sized to receive a single use disposable bottle with a flat handle portion, wherein the eye guide is an oval ring having a support flange attached to a back surface of the eye guide.

2. The device as in claim 1 wherein the base portion is substantially perpendicular to the extension portion.

3. A method for applying ophthalmic solutions by:

attaching a bottle guide that is comprised of an eye guide, a substantially rigid extension portion attached at a first end to the eye guide, and a bottle attaching portion having a slit and attached to a second end of the extension portion to a bottle with a flat handle portion, wherein the eye guide is an oval ring having a support flange attached to a back surface of the eye guide, placing the eye guide around an eye contained in a head;

tilting the head backward and looking up at a dispensing portion of the bottle, gently applying drops of ophthalmic solution to the eye; and removing the bottle guide from the proximity of the face.

4. The method of claim 3, wherein said bottle attaching portion further comprises a base portion that is substantially perpendicular to the extension portion.

* * * * *